United States Patent [19]

Brooks et al.

[11] Patent Number: 5,220,059
[45] Date of Patent: Jun. 15, 1993

[54] LIPOXYGENASE-INHIBITING COMPOUNDS DERIVED FROM NON-STEROIDAL ANTIINFLAMMATORY CARBOXYLIC ACIDS

[75] Inventors: Dee W. Brooks, Libertyville; Joseph F. Dellaria, Jr., Lindenhurst; James B. Summers, Jr., Libertyville, all of Ill.

[73] Assignee: Abbott Laboratories, Abbott Park, Ill.

[21] Appl. No.: 511,380

[22] Filed: Apr. 19, 1990

[51] Int. Cl.$^5$ ............... C07D 83/08; C07D 83/10; A61K 31/325
[52] U.S. Cl. ............... 562/623; 560/24; 558/232; 564/26; 564/56
[58] Field of Search ............... 548/492; 558/232; 560/24; 564/26, 56; 514/420, 482, 485, 622; 562/623

[56] References Cited

U.S. PATENT DOCUMENTS

| | | | |
|---|---|---|---|
| 3,388,153 | 6/1968 | Johnson | 562/623 |
| 4,156,739 | 5/1979 | Fountain et al. | 562/623 |
| 4,412,994 | 11/1983 | Sloan et al. | 514/420 |
| 4,760,057 | 7/1988 | Alexander | 560/24 |
| 4,874,759 | 10/1989 | Tahara et al. | 548/492 |
| 5,026,729 | 6/1991 | Brooks et al. | 562/623 |

*Primary Examiner*—David B. Springer
*Attorney, Agent, or Firm*—Jerry F. Janssen

[57] ABSTRACT

Compounds of the formula:

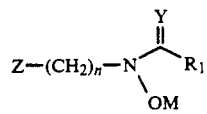

wherein
$R_1$ is selected from (1) hydrogen; (2) $-NR_2R_3$, $-OR_2$ or $-SR_2$ where $R_2$ and $R_3$ are independently selected from hydrogen, alkyl, aryl and alkylaryl; and (3) optionally substituted C1-C8 alkyl, C2-C8 alkenyl, arylalkyl or cycloalkyl;
Y is selected from sulfur and oxygen;
n is an integer selected from 0 and 1;
M is hydrogen, a pharmaceutically acceptable cation, or a metabolically cleavable group; and
Z is a residue of a non-steroidal antiinflammatory drug of general form Z—COOH;
or a pharmaceutically acceptable salt, ester or prodrug thereof,
as well as pharmaceutical compositions containing the above compounds and a method for their use as lipoxygenase inhibitors.

6 Claims, No Drawings

LIPOXYGENASE-INHIBITING COMPOUNDS DERIVED FROM NON-STEROIDAL ANTIINFLAMMATORY CARBOXYLIC ACIDS

TECHNICAL FIELD

The invention relates to organic compounds which inhibit lipoxygenase enzymes and to prodrug derivatives thereof having metabolically cleavable groups, as well as to pharmaceutical compositions containing such compounds and their use in the inhibition of lipoxygenase enzymes in humans and animals. More particularly, the invention pertains to lipoxygenase-inhibiting compounds which are derived from non-steroidal antiinflammatory drugs (NSAIDs) which contain a carboxylic acid functionality.

BACKGROUND OF THE INVENTION

Lipoxygenase enzymes catalyze the conversion of arachidonic acid into a number of biologically active products, including the leukotrienes and 5-hydroeicosatetraenoic acid (5-HETE). A variety of biological effects are associated with these products of lipoxygenase metabolism of arachidonic acid, and several have been implicated as important mediators in various pathophysiological states. For example, the leukotrienes $LTC_4$ and $LTD_4$ are potent constrictors of human airways in vitro, and aerosol administration of these substances to non-asthmatic volunteers induces broncho-constriction.

On the other hand, 5-HETE and the leukotriene $LTB_4$ are potent chemotactic factors for inflammatory cells such as polymorphonuclear leukocytes, and have been found in the synovial fluid of rheumatoid arthritic patients. Leukotrienes have also been implicated as important mediators in asthma, atherosclerosis, rheumatoid arthritis, gout, psoriasis, acne, allergic rhinitis, adult respiratory distress syndrome, Crohn's disease, endotoxin shock, inflammatory bowel disease, ischemia-induced myocardial injury and central nervous system pathophysiology, among others. The biological activity of the leukotrienes has been reviewed by Lewis and Austen, *J. Clinical Invest.* 73:889 (1984), and by J. Sirois, *Adv. Lipid Res.* 21:78 (1985).

Lipoxygenase enzymes are thus believed to play an important role in the mediation of asthma, allergy, arthritis, psoriasis, inflammation and other pathologies. Because inhibition of the lipoxygenase enzymes blocks the biosynthesis of these mediators, lipoxygenase inhibitors are expected to provide an effective means for the systemic and/or symptomatic treatment of these diseases.

SUMMARY OF THE INVENTION

The compounds of the present invention, which exhibit unexpected activity as inhibitors of lipoxygenase enzymes and in particular of 5-lipoxygenase, include compounds having the following formula:

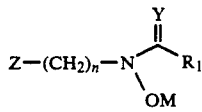
(Formula I)

as well as pharmaceutically acceptable salts and prodrugs thereof. In the above compounds, $R_1$ is selected from (1) hydrogen; (2) $-NR_2R_3$, $-OR_2$ or $-SR_2$ where $R_2$ and $R_3$ are independently selected from hydrogen, alkyl, aryl and alkylaryl; and (3) C1-C8 alkyl, C2-C8 alkenyl, arylalkyl or cycloalkyl. Groups (3) are optionally substituted by one or more substituents independently selected from C1-C6 alkoxy, halo, cyano, amino, carboxy, $-COX$, $-OCOX$ and $-NHCOX$ where X is selected from alkoxy, amino, alkylamino, dialkylamino, alkyl and aryl.

Also, in the above compounds, Y is sulfur or oxygen and M is hydrogen, a pharmaceutically acceptable cation, or a metabolically cleavable group such as aroyl, C1-C12 alkoyl, tetrahydropyran, methoxymethyl, trimethylsilyl, alkoxycarbonyl, glutaryl, succinyl or carbamoyl. The number of alkylene radicals, n, is either 0 or 1. Additionally, Z is the residue of a compound selected from the non-steroidal antiinflammatory drugs containing a carboxylic acid group, of the general form Z—COOH.

The compositions of the present invention comprise a pharmaceutically acceptable carrier in combination with a therapeutically effective amount of one of the above inventive compounds.

The methods of the present invention include the use of the above compounds in the treatment of asthma, rheumatoid arthritis, gout, psoriasis, allergic rhinitis, adult respiratory distress syndrome, Crohn's disease, endotoxin shock, inflammatory bowel disease, ischemia-induced myocardial injury or central nervous system pathophysiology in a mammal in need of such treatment.

DETAILED DESCRIPTION OF THE INVENTION

The present invention provides derivatives of non-steroidal antiinflammatory drugs (NSAIDs) and pharmaceutically acceptable salts, esters and prodrugs thereof, as well as the use of these compounds as lipoxygenase inhibitors and compositions containing them. The inventive compounds are those having the structural formula:

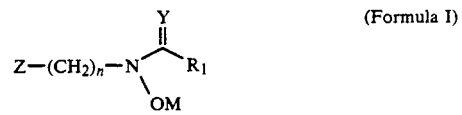
(Formula I)

wherein $R_1$ is chosen from (1) hydrogen; (2) $-NR_2R_3$, $-OR_2$ or $-SR_2$ where $R_2$ and $R_3$ are independently selected from hydrogen, alkyl, aryl and alkylaryl; and (3) C1-C8 alkyl, C2-C8 alkenyl, arylalkyl and cycloalkyl, which groups are optionally substituted by one or more substituents independently selected from C1-C6 alkoxy, halo, cyano, amino, carboxy, $-COX$, $-OCOX$ and $-NHCOX$ where X is selected from alkoxy, amino, alkylamino, dialkylamino, alkyl, aryl.

Moreover, in Formula I, n is either 0 or 1; Y is S or O; and M is hydrogen, a pharmaceutically acceptable cation, or a metabolically cleavable group selected from aroyl, C1-C12 alkoyl, tetrahydropyran, methoxymethyl, trimethylsilyl, alkoxycarbonyl, glutaryl, succinyl or carbamoyl.

Z in the above formula is a residue of a compound selected from the non-steroidal antiinflammatory drugs containing a carboxylic acid group and having the general form Z—COOH.

Compounds considered within the classification of non-steroidal antiinflammatory drugs (NSAIDs) have been documented by J. Lombardino in "Nonsteroidal Antiinflammatory Drugs", Wiley-Interscience, New York (1985). The NSAIDs utilized in the present invention which are of the general form Z—COOH include, but are not limited to, the following examples:
(1) benoxaprofen,
(2) benzofenac,
(3) bucloxic acid,
(4) butibufen,
(5) carprofen,
(6) cicloprofen,
(7) cinmetacin,
(8) clidanac,
(9) clopirac,
(10) diclofenac,
(11) etodolac,
(12) fenbufen,
(13) fenclofenac,
(14) fenclorac,
(15) fenoprofen,
(16) fentiazac,
(17) flunoxaprofen,
(18) furaprofen,
(19) furobufen,
(20) furofenac,
(21) ibufenac
(22) ibuprofen,
(23) indomethacin,
(24) indoprofen,
(25) isoxepac,
(26) ketoprofen,
(27) lonazolac,
(28) metiazinic,
(29) miroprofen,
(30) naproxen,
(31) oxaprozin,
(32) oxepinac,
(33) pirprofen,
(34) pirazolac,
(35) protizinic acid,
(36) sulindac,
(37) suprofen,
(38) tiaprofenic acid,
(39) tolmetin, and
(40) zomepirac.

Examples of compounds which are representative of the compounds of the present invention include, but which are not intended to limit the scope of the claimed invention, include:
N-hydroxy-N-[1-(4-(2'-methylpropyl)phenyl)ethyl] urea,
N-hydroxy-N-1-(6-methoxynaphthalen-2-yl)ethyl urea,
N'-methyl-N-hydroxy-N-1-(4-(2'-methylpropyl)phenyl)ethyl urea,
N'-methyl-N-hydroxy-N-1-(6-methoxynaphthalen-2-yl)ethyl urea,
N-hydroxy-N-1-(6-methoxynaphthalen-2-yl)ethyl acetamide,
N-hydroxy-N-1-(6-methoxynaphthalen-2-yl)ethyl acetamide potassium salt,
N-hydroxy-N-1-(6-methoxynaphthalen-2-yl)ethyl urea potassium salt,
N-hydroxy-N-1-(6-methoxynaphthalen-2-yl)ethyl ethoxycarbamate,
N-hydroxy-N-1-(6-methoxynaphthalen-2-yl)ethyl tert-butylthiolcarbamate,
N-hydroxy-N-1-(6-methoxynaphthalen-2-yl)ethyl thiourea,
N-hydroxy-N-1-(6-methoxynaphthalen-2-yl)ethyl-N'-phenyl urea,
N-hydroxy-N-1-(6-methoxynaphthalen-2-yl)ethyl-N'-benzyl urea,
N-benzoyloxy-N-1-(6-methoxynaphthalen-2-yl)ethyl urea,
N-trimethylsilyloxy-N-1-(6-methoxy-naphthalen-2-yl)ethyl urea,
N-hydroxy-N-1-(6-methoxynaphthalen-2-yl)ethyl thioacetamide,
N-hydroxy-N-[2-(N-(4-chlorobenzoyl)-5-methoxy-2-methyl-[1H]-indol-3-yl)ethyl] urea,
N-hydroxy-N-[2-(4-(2-methylpropyl)phenyl)propyl] urea,
N-hydroxy-N-[2-(4-benzyloxy-3-chlorophenyl)ethyl] urea,
N-hydroxy-N-[1-(4-(2'-methylpropyl)phenyl)propyl] urea,
N-hydroxy-N-[2-(4-(2-methylpropyl)phenyl)butyl] urea,
N-hydroxy-N-fluoren-2-ylethyl urea,
N-hydroxy-N-[2-(N-cinnamoyl-5-methoxy-2-methyl-[1H]-indol-3-yl)ethyl] urea,
N-hydroxy-N-(6-chloro-5-phenylindanyl) urea,
N-hydroxy-N-[2-(2-(2,4-dichlorophenoxyphenyl))ethyl] urea,
N-hydroxy-N-(4-phenoxyphenyl)ethyl urea,
N-hydroxy-N-(3-phenylbenzo[b]furan-7-yl)ethyl urea,
N-hydroxy-N-[2-(2,3-dihydro-2-ethylbenzo[b]furan-5-yl)-ethyl] urea,
N-hydroxy-N-(4-(N-1,3-dihydro-1-oxoisoindolyl)-phenyl)ethyl urea,
N-hydroxy-N-[1-(4-(2'-methylpropyl)phenyl)ethyl] thiourea,
N-hydroxy-N-[1-(4-(2'-methylpropyl)phenyl)ethyl] ethoxycarbamate,
N-hydroxy-N-[1-(4-(2'-methylpropyl)phenyl)ethyl] thioethylcarbamate,
N-hydroxy-N-[2-(N-(4-chlorobenzoyl)-5-methoxy-2-methyl-[1H]-indol-3-yl)ethyl]-N'-methyl urea,
N-hydroxy-N-[1-(4-(2'-methylpropyl)phenyl)ethyl] cyclopropylcarboxyamide,
N-hydroxy-N-[1-(4-(2'-methylpropyl)phenyl)ethyl] cyclohexylcarboxyamide,
N-hydroxy-N-[1-(4-(2'-methylpropyl)phenyl)ethyl] 4-butenylcarboxyamide,
N-hydroxy-N-[1-(4-(2'-methylpropyl)phenyl)ethyl] 4-methoxycarbonyl-cyclohexylcarboxyamide,
N-hydroxy-N-[1-(4-(2'-methylpropyl)phenyl)ethyl] 4-carboxy-cyclohexylcarboxyamide,
N-hydroxy-N-[1-(4-(2'-methylpropyl)phenyl)ethyl] 4-chloro-cyclohexylcarboxyamide,
N-hydroxy-N-[1-(4-(2'-methylpropyl)phenyl)ethyl] 4-cyano-cyclohexylcarboxyamide,
N-hydroxy-N-[1-(4-(2'-methylpropyl)phenyl)ethyl] 4-acetoxy-cyclohexylcarboxyamide,
N-hydroxy-N-[1-(4-(2'-methylpropyl)phenyl)ethyl] 4-amino-cyclohexylcarboxyamide,
N-hydroxy-N-[1-(4-(2'-methylpropyl)phenyl)ethyl] 4-methoxy-cyclohexylcarboxyamide,
N-hydroxy-N-[1-(4-(2'-methylpropyl)phenyl)ethyl] 4-acetamido-cyclohexylcarboxyamide,
N-hydroxy-N-[1-(6-methoxynaphthalen-2-yl)ethyl] benzylcarboxyamide,
N-hydroxy-N-[1-(6-methoxynaphthalen-2-yl)ethyl] 4-methoxycarbonyl-benzylcarboxyamide,
N-hydroxy-N-[1-(6-methoxynaphthalen-2-yl)ethyl] 4-carboxy-benzylcarboxyamide, N-hydroxy-N-[1-(6-methoxynaphthalen-2-yl)ethyl] 4-chloro-benzylcarboxyamide,
N-hydroxy-N-[1-(6-methoxynaphthalen-2-yl)ethyl] 4-cyano-benzylcarboxyamide,
N-hydroxy-N-[1-(6-methoxynaphthalen-2-yl)ethyl] 4-acetoxy-benzylcarboxyamide,
N-hydroxy-N-[1-(6-methoxynaphthalen-2-yl)ethyl] 4-amino-benzylcarboxyamide,
N-hydroxy-N-[1-(6-methoxynaphthalen-2 yl)ethyl] 4-methoxy-benzylcarboxyamide, and
N-hydroxy-N-[1-(6-methoxynaphthalen-2-yl)ethyl] 4-acetamido-benzylcarboxyamide.

Especially preferred compounds of the present invention include, but are not limited to, the following:
N-hydroxy-N-1-(6-methoxynaphthalen-2-yl)ethyl urea,
N-hydroxy-N-[2-(N-(4-chlorobenzoyl)-5-methoxy-2-methyl-[1H]-indol-3-yl)ethyl] urea, and
N-hydroxy-N-[2-(4-(2-methylpropyl)phenyl)propyl] urea.

It will be recognized that the compounds of the present invention may contain one or more asymmetric carbon atoms. It is to be understood that R and S isomers and racemic and other mixtures thereof, as well as both cis and trans isomers, are contemplated by this invention and are intended to be within the scope of the claims hereinbelow.

The term "alkenyl" is used herein to mean a straight or branched chain unsaturated radical of 2 to 12 carbon atoms including, but not limited to, ethenyl, 1-propenyl, 2-propenyl, 2-methyl-1-propenyl, 1-butenyl and 2-butenyl.

The term "alkenylene" is used herein to mean a straight or branched-chain unsaturated divalent radical including, but not limited to, —CH=CH—, —CH=CHCH$_2$—, —CH=CHCH(CH$_3$)—, —C(CH$_3$)=CHCH$_2$—, —CH$_2$CH=CHCH$_2$— and —C(CH$_3$)$_2$CH=CHC(CH$_3$)$_2$—.

The term "alkoxy" is used herein to mean —OR$_8$ wherein R$_8$ is an alkyl radical including, but not limited to, methoxy, ethoxy, isopropoxy, n-butoxy, sec-butoxy, isobutoxy and tert-butoxy.

The term "alkoyl" is used herein to mean —C(O)R$_{10}$ wherein R$_{10}$ is an alkyl radical including, but not limited to, formyl, acetyl, propionyl, butyryl, isobutyryl and pivaloyl.

The term "alkyl" is used herein to mean a straight or branched chain radical of 1 to 12 carbon atoms including, but not limited to, methyl, ethyl, n-propyl, isopropyl, n-butyl, sec-butyl, isobutyl and tert-butyl.

The term "alkylene" is used herein to mean a straight or branched-chain divalent radical such as —CH$_2$—, —CHCH$_3$—, —C(CH$_3$)$_2$—, —CH(C$_2$H$_5$)—, —CH$_2$CH$_2$—, —CH$_2$CHCH$_3$—, —C(CH$_3$)$_2$C(CH$_3$)$_2$— and —CH$_2$CH$_2$CH$_2$—.

The term "alkylsulfonyl" is used herein to mean —SO$_2$R$_{16}$ wherein R$_{16}$ is an alkyl radical including, but not limited to, methylsulfonyl (i.e. mesityl), ethyl sulfonyl an isopropylsulfonyl.

The term "aroyl" is used herein to mean —C(O)R$_{12}$ wherein R$_{12}$ is an aryl radical including, but not limited to, benzoyl, 1-naphthoyl and 2-naphthoyl.

The term "aryl" is used herein to mean a substituted or unsubstituted carbocyclic or heterocylic aromatic radical wherein the substituents are chosen from halo, nitro, cyano, C1-C12 alkyl, alkoxy, and halosubstituted alkyl including, but not limited to, phenyl, 1- or 2-naphthyl, 2-, 3-, or 4-pyridyl, 2- or 3-furyl, 2- or 3-thienyl, and 2-, 4- or 5-thiazoyl.

The term "arylalkenyl" is used herein to mean an aryl group appended to an alkenyl radical including, but not limited to, phenylethenyl, 3-phenylprop-1-enyl, 3-phenylprop-2-enyl and 1-naphthylethenyl.

The term "arylalkoxy" is used herein to mean —OR$_{14}$ wherein R$_{14}$ is an arylalkyl radical including, but not limited to, phenylmethoxy (i.e., benzyloxy), 4-fluorobenzyloxy, 1-phenylethoxy, 2-phenylethoxy, diphenylmethoxy, 1-naphthylmethoxy, 2-napthylmethoxy, 9-fluorenoxy, 2-, 3- or 4-pyridylmethoxy and 2-, 3-, 4-, 5-, 6-, 7-, or 8-quinolylmethoxy.

The term "arylalkyl" is used herein to mean an aryl group appended to an alkyl radical including, but not limited to, phenylmethyl (benzyl), 1-phenylethyl, 2-phenylethyl, 1-naphthylethyl and 2-pyridylmethyl.

The term "aryloxy" is used herein to mean —OR$_{13}$ wherein R$_{13}$ is an aryl radical including, but not limited to, phenoxy, 1-naphthoxy and 2-naphthoxy.

The term "arylthioalkoxy" is used herein to mean —SR$_{15}$ wherein R$_{15}$ is an arylalkyl radical including, but not limited to, phenylthiomethoxy i.e., thiobenzyloxy), 4-fluorothiobenzyloxy, 1-phenylthioethoxy, 2-phenylthioethoxy, diphenylthiomethoxy and 1-naphthylthiomethoxy.

The term "carboalkoxy" is used herein to mean —C(O)R$_{11}$ wherein R$_{11}$ is an alkoxy radical including, but not limited to, carbomethoxy, carboethoxy, carboisopropoxy, carbobutoxy, carbosec-butoxy, carboisobutoxy and carbotert-butoxy.

The term "carboxyalkyl" is used herein to mean an alkyl radical of 1 to 11 carbon atoms bearing a carboxyl group including, but not limited to, carboxymethyl and carboxypropyl.

The term "cycloalkyl" is used herein to mean a cyclic radical of 3 to 8 carbon atoms including, but not limited to, cyclopropyl, cyclobutyl, cyclopentyl and cyclohexyl.

The terms "halo" and "halogen" are used herein to mean a radical derived from one of the elements fluorine, chlorine, bromine, and iodine.

The term "halosubstituted alkyl" refers to an alkyl radical substituted with one or more halogens including, but not limited to, chloromethyl, trifluoromethyl and 2,2,2-trichloroethyl.

The term "lipoxygenase" is used herein to mean 5- and/or 12-lipoxygenase, the enzymes which oxidize arachidonic acid at the 5 and 12 positions, respectively.

The term "metabolically cleavable group" is used herein to mean a moiety which is readily cleaved in vivo from the compound bearing it, which compound, after cleavage, remains or becomes physiologically active including, but not limited to, acetyl, ethoxycarbonyl, methoxycarbonyl, tert-butoxycarbonyl, glutaryl, succinyl and carbamoyl.

The term "pharmaceutically acceptable cation" refers to relatively non-toxic cations including, but not limited to, cations based on the alkali and alkaline earth metals including, but not limited to, sodium, lithium, potassium, calcium and magnesium, as well as relatively non-toxic ammonium, quaternary ammonium, and amine cations including, but not limited to, ammonium, tetramethylammonium, tetraethylammonium, methylamine, dimethylamine, trimethylamine, triethylamine and ethylamine.

The term "thioalkoxy" is used herein to mean —SR$_9$ wherein R$_9$ is an alkyl radical including, but not limited to, thiomethoxy, thioethoxy, thioisopropoxyyl, n-thiobutoxy, sec-thiobutoxy, isothiobutoxy and tert-thiobutoxy.

Compounds of the invention which have metabolically cleavable groups may act as prodrugs of lipoxygenase inhibitors as they are converted in vivo to active lipoxygenase-inhibiting residues. Moreover, as prodrugs the compounds of the present invention may exhibit improved bioavailability as a result of enhanced solubility, rate of absorbtion and/or duration of action.

The compounds of the present invention can also be prepared in the form of pharmaceutically acceptable salts, esters and other prodrugs. Derivative salts include relatively non-toxic inorganic or organic acid addition salts or alkaline earth metal salts of the inventive compounds, which can be prepared in situ during the final isolation and purification of the compounds or by separately reacting the compound in its free base or acid form with a suitable organic or inorganic acid or base, respectively. Where the compounds include a basic functionality such as an amine or alkylamine, representative salts include hydrochloride, sulfate, acetate, maleate, lauryl sulphate and the like. Where an acidic functionality is present, salts such as sodium, calcium, potassium and magnesium salts may be formed. Further examples may be found in Berge, et al., "Pharmaceutical Salts", *J. Pharm. Sci.* 66:1-19 (1977).

Pharmaceutically acceptable esters and other prodrugs of the inventive compounds can be prepared by methods known in the art, such as those described in "Design of Prodrugs", Bundgaard, H., ed., Elsevier, Amsterdam, 1-92 (1985). These prodrugs, which are formed by the addition of a metabolically cleavable group to compounds bearing a hydroxyl or carboxyl functionality, are converted in vivo to the parent compound and may provide improved absorption and bioavailability. Examples of such esters include glycyl, lysyl, acetyl and succinyl derivatives, while other prodrugs may be formed by the addition, for example, of alkanoyl, aroyl, aminocarbonyl, alkylamincarbonyl, alkoxycarbonyl and silyl groups.

Method of Treatment

The method of the present invention provides for the inhibition of 5- and/or 12-lipoxygenase activity in a human or lower animal host in need of such treatment, which method comprises administering to the human or lower animal host a therapeutically effective amount of one of the inventive compounds to inhibit lipoxygenase activity in the host. The compounds of the present invention may be administered orally, parenterally or topically in unit dosage formulations containing conventional nontoxic pharmaceutically acceptable carriers, adjuvants and vehicles as desired.

The term "parenterally" as used herein includes subcutaneous, intravenous, intra-arterial injection or infusion techniques, without limitation. The term "topically" encompasses administration rectally, vaginally and by inhalation spray, as well as by the more common routes of the skin and the mucous membranes of the mouth and nose.

Total daily dose of the compounds of this invention administered to a host in single or divided doses may be in amounts, for example, of from about 0.001 to about 100 mg/kg body weight daily and more usually 0.1 to 35 mg/kg/day. Unit dosage compositions may contain such amounts of such submultiples thereof as may be used to make up the daily dose. It will be understood, however, that the specific dose level for any particular patient will depend upon a variety of factors including body weight, general health, sex, diet, time and route of administration, rates of absorption and excretion, combination with other drugs and the severity of the particular disease being treated.

Formulation

The pharmaceutical compositions of the present invention comprise a compound of this invention and one or more nontoxic pharmaceutically acceptable carriers, adjuvants or vehicles in unit dosage form suitable for the inhibition of 5- or 12-lipoxygenase activity in a human or lower animal host in need of such treatment. The amount of active ingredient that may be combined with such materials to produce a single dosage form will vary depending upon various factors, as indicated above.

A variety of materials can be used as carriers, adjuvants and vehicles in the composition of this invention, as available in the pharmaceutical arts. Injectable preparations, such as oleaginous solutions, suspensions or emulsions may be formulated according to known art using suitable dispersing or wetting agents and suspending agents, as needed. The sterile injectable preparation may employ a nontoxic parenterally acceptable diluent or solvent as, for example, sterile nonpyrogenic water or 1,3-butanediol.

Among the other acceptable vehicles and solvents that may be employed are 5% dextrose injection, Ringer's injection and isotonic sodium chloride injection (as described in the USP/NF). In addition, sterile, fixed oils are conventionally employed as solvents or suspending media. For this purpose any bland fixed oil may be used, including synthetic mono-, di- or triglycerides. Fatty acids such as oleic acid can also be used in the preparation of injectable compositions.

Suppositories for rectal or vaginal administration of the compounds of this invention can be prepared by mixing the drug with suitable nonirritating excipients such as cocoa butter and polyethylene glycols, which are solid at ordinary temperatures but liquid at body temperature and which therefore melt in the rectum or vagina and release the drug.

Solid dosage forms for oral administration include capsules, tablets, pills, troches, lozenges, powders and granules. In such solid dosage forms, the active compound may be admixed with at least one inert diluent such as sucrose, lactose or starch. Such dosage forms may also comprise, as is normal practice, pharmaceutical adjuvant substances, e.g., stearate lubricating agents. In the case of capsules, tablets and pills, the dosage forms may also comprise buffering agents. Solid oral preparations can also be prepared with enteric or other coatings which modulate release of the active ingredients.

Liquid dosage forms for oral administration include pharmaceutically acceptable emulsions, solutions, suspensions, syrups and elixirs containing inert nontoxic diluents commonly used in the art, such as water and alcohol. Such compositions may also comprise adjuvants, such as wetting, emulsifying, suspending, sweetening, flavoring and perfuming agents.

Synthesis of Compounds

The compounds of the present invention can be prepared by the processes presented hereinbelow. In certain cases where the non-steroidal antiinflammatory drug (NSAID) contains functional groups which might interfere with the desired transformation outlined in the following processes, it is recognized that common methods of protection of these groups followed by deprotection at a later stage in the preparation of the desired product can be employed. A general reference source for methods of protection and deprotection is T. W. Greene, "Protective Groups in Organic Synthesis", Wiley-Interscience, New York (1981).

In the synthetic processes of Schemes 1 and 2 below, a sequence of reactions converts the carboxylic acid function found in the representative examples of NSAIDs into a hydroxylamine or a methylenehydroxylamine function, respectively. These intermediates are then further elaborated to provide the novel compounds of the present invention.

Scheme 1 summarizes a method for transforming an NSAID carboxylic function into a hydroxylamine.

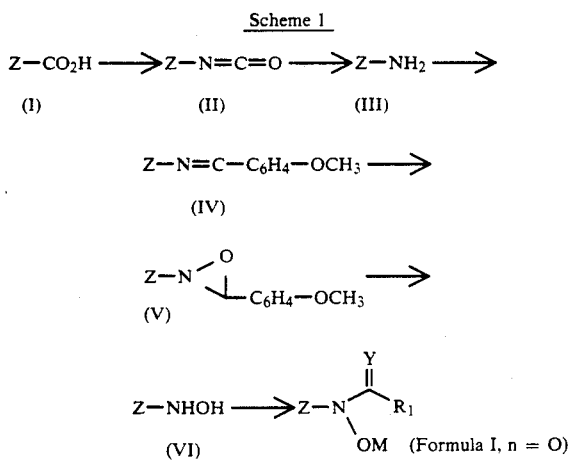

In the first step of this process, the carboxylic acid I is converted into the corresponding amine III by a known method such as isocyanate II formation. The isocyanate II may be formed by, for example, the method reported by Ninamiya et al., *Tetrahedron* 30:2151 (1974), or by treating the carboxylic acid with thionyl chloride or oxalyl chloride to provide the corresponding acid chloride, Z—COCl, reacting the acid chloride with an azide salt to form the acylazide intermediate, Z—CON$_3$, and heating to provide the isocyanate intermediate II. Subsequent hydrolysis of the isocyanate provides the desired amine, Z—NH$_2$. The amine III is then subjected to an oxidative procedure which is adapted from a method described by Gundke et al., *Synthesis* 12:1115 (1987). The amine III is converted to an imine IV by treatment with p-anisaldehyde which is then reacted with a hydroperoxyacid, such as 3-chloroperoxybenzoic acid, to provide an oxaziridine V. Treatment of this oxaziridine intermediate with hydroxylamine hydrochloride provides the desired hydroxylamine VI.

Scheme 2, below, summarizes a method for converting the carboxylic function of an NSAID into the corresponding methylenehydroxylamine.

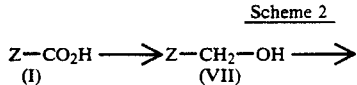

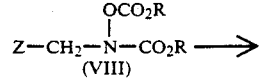

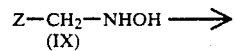

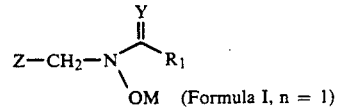

In the first step, the carboxylic acid I is reduced to the corresponding alcohol VII. A bis-protected form of the desired hydroxylamine is then prepared by reaction of the alcohol VII with a N,O-bis-acylhydroxyl-amine as described by Mitsunobu, *Synthesis* 1 (1981) to provide VIII (R=t-butyl or benzyl). The intermediate VIII with R=t-butyl is deprotected by brief exposure to equal volumes trifluoroacetic acid and dichloromethane to provide the unprotected methylenehydroxylamine IX. Alternatively, when R=benzyl, deprotection is achieved by exposure of vIII to trimethylsilyl iodide in anhydrous dichloromethane.

The hydroxylamines VI and IX can be readily converted to the desired compounds of Formula I by known methods. For example, reaction of a hydroxylamine with trimethylsilylisocyanate and subsequent aqueous workup provides the desired N-hydroxyurea compounds of Formula I wherein R$_1$=NH$_2$. In a similar manner, the utilization of a substituted isocyanate, R$_2$—N=C=O, provides N-hydroxyurea compounds of Formula I wherein Y=O and R$_1$=NHR$_2$. The hydroxylamines can be converted to compounds of Formula I wherein Y=O and R$_1$=hydrogen by treatment with an alkoxyformate, and to compounds of Formula I wherein Y=O and R$_1$=OR$_2$ by treatment with the requisite alkoxycarbonate or alkoxychloroformate. The hydroxylamines can be converted to compounds of Formula I wherein Y=O and R$_1$=alkyl, alkenyl, arylalkyl, cycloalkyl or substituted derivatives thereof by treatment with the requisite acylchloride or acid anhydride. The hydroxylamines can be converted to the compounds of Formula I wherein Y=O and R$_1$=SR$_2$ by treatment with the requisite thioalkoxycarbonate or thioalkoxychloroformate. The hydroxylamines can be converted to compounds of Formula I wherein Y=S by using thiocarbonyl reagents in a manner analogous to that of the previously described methods.

The following Examples are for the purpose of better illustrating the preparation of the compounds of the present invention, and are not intended to limit the specification or claims in any manner whatsoever.

EXAMPLE 1

N-hydroxy-N-[1-(4-2'-methylpropyl)phenyl)ethyl] urea (Formula 1, Z=1-(4-(2'-methylpropyl)phenyl)ethyl, R$_1$=NH$_2$, M=H, Y=O)

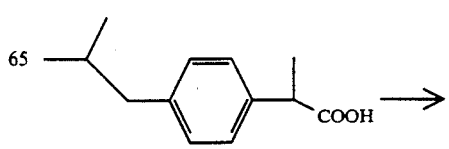

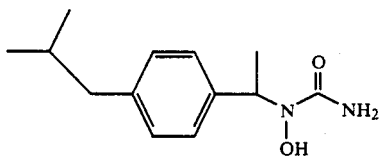

A representative compound of the present invention was prepared according to Scheme 1 in the following manner. To a solution of ibuprofen (10.0 g, 50 mmole) in 100 mL of benzene were added triethylamine (6.8 mL, 50 mmole) and diphenylphosphoryl azide (10.6 mL, 50 mmole). The solution was heated to reflux and stirred for one hour. To this solution was added tert-butanol (9.1 mL, 0.10 mole) via syringe and the reaction mixture stirred for four hours at 78° C. The solution was cooled to room temperature and quenched with 10% HCl solution (50 mL). The reaction mixture was extracted with ethyl acetate (3×75 mL) and the organic extracts were washed, first with saturated sodium bicarbonate solution (75 mL) and then with brine (75 mL). The solution was dried (MgSO₄), filtered and concentrated to give 10.4 g of crude product as an oil. The above crude material (10.5g, 37.5 mmole) was placed in 20 mL of 4N HCl-dioxane solution at 0° C. The solution was warmed to room temperature and stirred for one hour. The solution was concentrated in vacuo and ether was added; the solution was the concentrated again to yield a white solid. The solid was filtered and washed with ether to yield 3.3 g of 1-(4-(2'-methylpropyl)phenyl)ethyl amine hydrochloride salt 1.1.

To a solution of the amine salt 1.1 (3.3 g, 15.5 mmole) in 15 mL methanol at room temperature were added p-anisaldehyde (1.9 mL, 15.5 mmole) and anhydrous sodium carbonate (2.5 g, 23.2 mmole). The mixture was stirred for 15 hours at room temperature and was filtered and concentrated to yield 6.4 g of the corresponding p-anisaldehyde imine 1.2.

The imine 1.2 (5.5 mmole) was dissolved in dry methylene chloride (12 mL) at −20° C., and a solution of 3-chloroperoxybenzoic acid (MCPBA, 85%; 2.7 g, 15.5 mmole) in dry methylene chloride (40 mL) was added dropwise. The solution was warmed to room temperature and stirred for eight hours. It was then quenched with saturated sodium bicarbonate solution (20 mL) and extracted with ethyl acetate (3×50 mL). The ethyl acetate extract was washed with brine, dried (MgSO₄), filtered and concentrated to give 6.5 g of the corresponding oxaziridine 1.3.

The oxaziridine 1.3 (15.5 mmole) was dissolved in methanol (50 mL) and hydroxylamine hydrochloride was added. The reaction was stirred for 14 hours at room temperature and was then concentrated in vacuo. Water was added to the residue and the oily 4-methoxybenzaldoxime was filtered off. The filtrate was extracted with ether (2×20 mL) and these extracts were discarded. The aqueous filtrate was basified with solid sodium bicarbonate to pH 8 (with gas being evolved) and was then extracted with ethyl acetate (3×50 mL). The ethyl acetate extract was dried over MgSO₄, filtered and concentrated to give 1.7 g of crude product. Chromatography (silica gel, 1:1 ether/hexanes) gave 0.72 g of the 1-(4-(2'-methylpropyl)phenyl)ethyl hydroxylamine 1.4.

To a solution of trimethylsilylisocyanate (1.2 mL, 7.46 mmole) in 5 mL THF was added the hydroxylamine 1.4 from above (0.72 g, 3.73 mmole) in 10 mL THF. After stirring thirty minutes, saturated ammonium chloride solution was added and the mixture was extracted with ethyl acetate (3×20 mL). The organic layer was washed with brine, dried (MgSO₄), filtered and concentrated. Chromatography (silica gel, 5% methanol/ether) gave 0.59 g of product which was slightly impure. Recrystallization from ethyl acetate/hexanes gave 0.39 g of desired product, N-hydroxy-N-[1-(4-(2'-methylpropyl)phenyl)ethyl]urea. m.p.=147° C.; ¹H NMR (300 MHz, DMSO-d₆); 9.02 (br s, 1H), 7.23 (d, J=8.5 Hz, 2H), 7.07 (d, J=9.0 Hz, 2H), 6.28 (br s, 2H), 5.26 (q, J=6.6, 14.1 Hz, 1H), 2.40 (d, J=6.3 Hz, 2H), 1.70 (m, 1H), 1.37 (d, J=7.5 Hz, 3H), 0.85 (d, J=6.2 Hz, 6H); MS (M+H)⁺ =237, (M+NH₄)⁺ =254. [Analysis calc'd for C₁₃H₂₀N₂O₂: C, 66.06; H, 8.54; N, 11.86; Found: C, 65.54; H, 8.39; N, 11.80.]

EXAMPLE 2

N-hydroxy-N-1-(6-methoxynaphthalen-2-yl)ethyl urea
(Formula 1, Z=1-(6-methoxynaphthalen-2-yl)ethyl,
R₁=NH₂, M=H, Y=O)

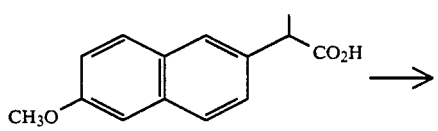

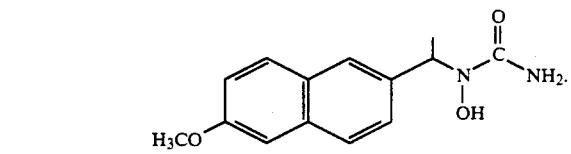

A further representative compound of the present invention was prepared according to Scheme 1 in the following manner. To a solution of naproxen (10.0 g, 0.04 mole) in 50 mL benzene at room temperature were added triethylamine (6.1 mL, 0.04 mole) and diphenylphosphoryl azide (9.4 mL, 0.04 mole). The solution was heated to reflux and stirred for two hours before slowly adding concentrated HCl solution (12 M; 7.2 mL, 0.08 mole) via pipet. Evolution of CO₂ gas was noted. The mixture was stirred at reflux for thirty minutes, then cooled to room temperature and concentrated in vacuo. Ether was added and the solution was concentrated again. A white solid precipitate was filtered and washed with ether to give 15.4 g of crude salt. Approximately 5.0 g of the salt was then placed in water and an insoluble gum was filtered off. The aqueous layer was basified with 2N NaOH solution and extracted with ethyl acetate (3×50 mL). The organic extract was washed with brine and dried (MgSO₄), filtered and concentrated in vacuo to give 2.51 g of the 1-(6-methoxynaphthalen-2-yl)ethyl amine hydrochloride salt 2.1 as a white solid.

To a solution of the amine 2.1 (2.51 g, 12.5 mmol) in 10 mL methanol were added p-anisaldehyde (1.5 mL, 12.5 mmol) and anhydrous sodium carbonate (1.3 g, 12.5 mmol). The mixture was stirred for 15 hours and was filtered through celite and concentrated to give 3.9 g of the corresponding p-anisaldehyde imine 2.2.

The imine 2.2 (12.2 mmole) was dissolved in 20 mL of methylene chloride and cooled to −20° C. To this was added MCPBA (85%; 2.5 g, 12.2 mmole) in dry methylene chloride (60 mL). The mixture was stirred for one hour at −20° C. The excess MCPBA was quenched with dimethylsulfide (0.4 mL). The reaction was quenched with saturated sodium bicarbonate solution and then extracted with ether (3×50 mL). The ether extract was dried over MgSO$_4$, filtered and concentrated to a volume of about 50 mL to provide a solution of the corresponding oxaziridine 2.3.

The above ether solution was diluted with 100 mL methanol followed by the addition of hydroxylamine hydrochloride (1.7 g, 24.4 mmole). The brown solution was stirred for one hour and was concentrated in vacuo. The residue was diluted with water and the oily 4-methoxybenzaldoxime was filtered off. The aqueous layer was acidified (2M HCl) and washed with ether (2x, 25 mL) and these extracts were discarded. The aqueous layer was carefully basified with 2N NaOH solution and extracted with ethyl acetate (3x, 50 mL). The organic layer was dried over MgSO$_4$, filtered and concentrated. Chromatography (silica gel, 20% ether/methylene chloride) gave 560 mg of 1-(6-methoxynaphthalen-2-yl)ethyl hydroxylamine 2.4.

To a solution of trimethylsilylisocyanate (0.82 mL, 5.15 mmol) in 5 mL of THF was added the hydroxylamine 2.4 from above (0.56 g, 2.58 mmol) in 10 mL THF. The reaction was stirred for thirty minutes and was quenched with saturated ammonium chloride solution. The mixture was extracted with ethyl acetate (3×30 mL). The organic extract was washed with brine and dried over MgSO$_4$, filtered and concentrated. The crude solid was filtered and washed with ether to give 0.47 g of the desired product, N-hydroxy-N-1-(6-methoxynaphthalen-2-yl)ethyl urea. m.p.=172.5°–173° C.; $^1$H NMR (300 MHz, DMSO-d$_6$) 9.07 (br s, 1H), 7.74 (m, 3H), 7.46 (dd, J=1.83, 11.41 Hz, 1H), 7.27 (d, J=2.94 Hz, 1H), 7.12 (dd, J=3.00, 9.01 Hz, 1H), 6.31 (br s, 2H), 5.44 (q, J=6.30, 13.51 Hz, 1H), 3.87 (s, 3H), 1.49 (d, J=6.60 Hz, 3H); MS (M+H)$^+$=261, (M+NH$_4$)$^+$=278. [Analysis calc'd for C$_{14}$H$_{16}$N$_2$O$_3$: C, 64.60; H, 6.20; N, 10.76; Found: C, 62.65; H, 6.03; N, 10.44.]

EXAMPLE 3

N'-methyl-N-hydroxy-N-1-(4-(2'-methylpropyl)phenyl)ethyl urea (Formula 1,
Z=1-(4-(2'-methylpropyl)phenyl)ethyl, R$_1$=NHCH$_3$, M=H, Y=O)

The above-named compound was prepared by the method of Example 1 except that the hydroxylamine (1.0 g, 5.17 mmole) was reacted with methylisocyanate (0.37 mL, 6.21 mmole) instead of trimethylsilylisocyanate to provide 0.68 g of the title compound after recrystallization from ethyl acetate/hexanes. m.p.=62° C.; $^1$H NMR (300 MHz, DMSO-d$_6$) 8.90 (s, 1 H), 7.23 (d, J=7.5 Hz, 2 H), 7.05 (d, J=7.5 Hz, 2 H), 6.8 (br q, J=3.5 Hz, 1 H), 5.23 (q, J=6.5 Hz, 1 H), 2.57 (d, J=3.5 Hz, 3 H), 2.40 (d, J=7.0 Hz, 2 H), 1.80 (nonet, J=7.0 Hz, 1 H) 1.38 (d, J=7.0 Hz, 3 H), 0.86 (d, J=7.0 Hz, 6 H); MS (M +H)$^+$=251.

EXAMPLE 4

N'-methyl-N-hydroxy-N-1-(6-methoxynaphthalen-2-yl)ethyl urea (Formula 1,
Z=1-(6-methoxynaphthalen-2-yl)ethyl, R$_1$=NHCH$_3$, M=H, Y=O)

The above-named compound was prepared by the method of Example 2 except that the hydroxylamine 2.4 (0.7 g, 3.22 mmole) was reacted with methylisocyanate (0.23 mL, 3.87 mmole) instead of trimethylsilylisocyanate to provide 0.57 g of the title compound after recrystallization from ethyl acetate/hexanes. m.p.=172.5° C.; $^1$H NMR (300 MHz, DMSO-d$_6$) 8.97 (s, 1 H), 7.7–7.8 (m, 3 H), 7.46 (dd, J=9.0, 1.5 Hz, 1 H), 7.27 (d, J=3.0 Hz, 1 H), 7.13 (dd, J=9.0, 3.0 Hz, 1 H), 6.83 (br q, J=4.5 Hz, 1 H), 5.40 (q, J=7.0 Hz, 1 H), 3.87 (s, 3 H), 2.58 (d, J=4.5 Hz, 3 H), 1.48 (d, J=7.0 Hz, 3 H); MS (M+NH$_4$)$^+$=292 and (M+H)$^+$=275. [Analysis calc'd for C$_{15}$H$_{18}$N$_2$O$_3$.0.1H$_2$O: C, 65.25; H, 6.64; N, 10.15; Found C, 65.05; H, 6.61; N, 10.02.]

EXAMPLE 5

N-hydroxy-N-1-(6-methoxynaphthalen-2-yl)ethyl acetamide (Formula 1,
Z=1-(6-methoxynaphthalen-2-yl)ethyl, R$_1$=CH$_3$, M=H, Y=O)

The above-named compound was prepared by treating a 25° C. THF solution (10 mL) of the hydroxylamine 2.4 (0.70 g, 3.22 mmole) sequentially with triethylamine (0.94 mL, 6.77 mmole) and acetyl chloride (0.48 mL, 6.77 mmole). The reaction was quenched with excess saturated aqueous NH$_4$Cl and the resulting two-phased mixture was extracted three times with ethyl acetate. The combined organic layers were washed with brine and dried over MgSO$_4$, filtered, and concentrated to provide the diacetate as a pink oil which partially solidified on standing. The unpurified mixture was dissolved in a 25 mL solution of 72:20:8 isopropanol:methanol:H$_2$O and treated with LiOH.H$_2$O (0.14 g, 3.22 mmole) and stirred at 25° C. for 1.5 hours. The reaction was quenched with excess saturated aqueous NH$_4$Cl and processed as described above. Recrystallization from ethyl acetate/hexanes provided 0.252 g of the title compound as a colorless solid. m.p.=176.5° C.; $^1$H NMR (300 MHz, DMSO-d$_6$) 9.52 (br s, 1 H), 7.72–7.85 (m, 3 H), 7.42 (dd, J=9.0, 1.5 Hz, 1 H), 7.28 (d, J=3 Hz, 1 H), 7.15 (dd, J=9.0, 3.0 Hz, 1 H), 5.75 (br m, 1 H), 3.86 (s, 3 H), 2.03 (s, 3 H), 1.53 (d, J=7.5 Hz, 3 H); MS (M+NH$_4$)$^+$=277 and (M+H)$^+$=260. [Analysis calc'd for C$_{15}$H$_{17}$NO$_3$: C, 69.48; H, 6.61; N, 5.40; Found: C, 69.48; H, 6.56; N, 5.37.]

EXAMPLE 6

N-hydroxy-N-1-(6-methoxynaphthalen-2-yl)ethyl acetamide potassium salt (Formula 1,
Z=1-(6-methoxynaphthalen-2-yl)ethyl, R$_1$=CH$_3$, M=K, Y=O)

The above-named compound is prepared using the product of Example 5 treated with one equivalent of potassium hydride in tetrahydrofuran and stirred at room temperature for 24 hours. The solvent is then removed to provide the desired product.

EXAMPLE 7

N-hydroxy-N-1-(6-methoxynaphthalen-2-yl)ethyl urea potassium salt (Formula 1,
Z=1-(6-methoxynaphthalen-2-yl)ethyl, R$_1$=NH$_2$, M=K, Y=O)

The above-named compound is prepared using the product of Example 2 treated with one equivalent of potassium hydride in tetrahydrofuran and stirred at room temperature for 24 hours. The solvent is then removed to provide the desired product.

EXAMPLE 8

N-hydroxy-N-1-(6-methoxynaphthalen-2-yl)ethyl ethoxycarbamate (Formula 1,
Z=1-(6-methoxynaphthalen-2-yl)ethyl, R₁=OEt, M=H, Y=O)

The above-named compound is prepared by treating the hydroxylamine 2.4 with ethoxycarbonyl chloride in dichloromethane.

EXAMPLE 9

N-hydroxy-N-1-(6-methoxynaphthalen-2-yl)ethyl tert-butylthiolcarbamate (Formula 1,
Z=1-(6-methoxynaphthalen-2-yl)ethyl, R₁=S-t-C₄H₉, M=H, Y=O)

The hydroxylamine 2.4 is treated with tert-butylthiolcarbonyl chloride in dichloromethane to provide the above-named compound.

EXAMPLE 10

N-hydroxy-N-1-(6-methoxynaphthalen-2-yl)ethyl thiourea (Formula 1,
Z=1-(6-methoxynaphthalen-2-yl)ethyl, R₁=NH₂, M=H, Y=S)

The above-named compound is prepared by the method of Example 2 except that trimethylsilylthiocyanate is used instead of trimethylsilylisocyanate.

EXAMPLE 11

N-hydroxy-N-1-(6-methoxynaphthalen-2-yl)ethyl-N'-phenyl urea (Formula 1,
Z=1-(6-methoxynaphthalen-2-yl)ethyl, R₁=NHC₆H₅, M=H, Y=S)

The above-named compound is prepared by the method of Example 2 except that phenylisocyanate is used instead of trimethylsilylisocyanate.

EXAMPLE 12

N-hydroxy-N-1-(6-methoxynaphthalen-2-yl)ethyl-N'-benzyl urea (Formula 1,
Z=1-(6-methoxynaphthalen-2-yl)ethyl, R₁=NHC₆H₅, M=H, Y=S)

The above-named compound is prepared by the method of Example 2 except that benzylisocyanate is used instead of trimethylsilylisocyanate.

EXAMPLE 13

N-benzoyloxy-N-1-(6-methoxynaphthalen-2-yl)ethyl urea (Formula 1,
Z=1-(6-methoxynaphthalen-2-yl)ethyl, R₁=NH₂, M=COC₆H₅, Y=O)

The above-named compound is prepared by treating the product of Example 2 with triethylamine and benzoyl chloride.

EXAMPLE 14

N-trimetylsilyloxy-N-1-(6-methoxynaphthalen-2-yl)ethyl urea (Formula 1,
Z=1-(6-methoxynaphthalen-2-yl)ethyl, R₁=NH₂, M=Si(CH₃)₃, Y=O)

The above-named compound is prepared by treating the product of Example 2 with trimethylsilylimidazole.

EXAMPLE 15

N-hydroxy-N-1-(6-methoxynaphthalen-2-yl)ethyl thioacetamide (Formula 1,
Z=1-(6-methoxynaphthalen-2-yl)ethyl, R₁=CH₃, M=H, Y=S)

The above-named compound is prepared by the method of Example 5 using thioacetic anhydride instead of acetylchloride.

EXAMPLE 16

N-hydroxy-N-[2-(N-(4-chlorobenzoyl)-5-methoxy-2-methyl-[1H]-indol-3-yl)ethyl] urea (Formula 1,
Z=2-(N-(4-chlorobenzoyl)-5-methoxy-2-methyl-[1H]-indol-3-yl)ethyl, R₁=NH₂, M=H, Y=O)

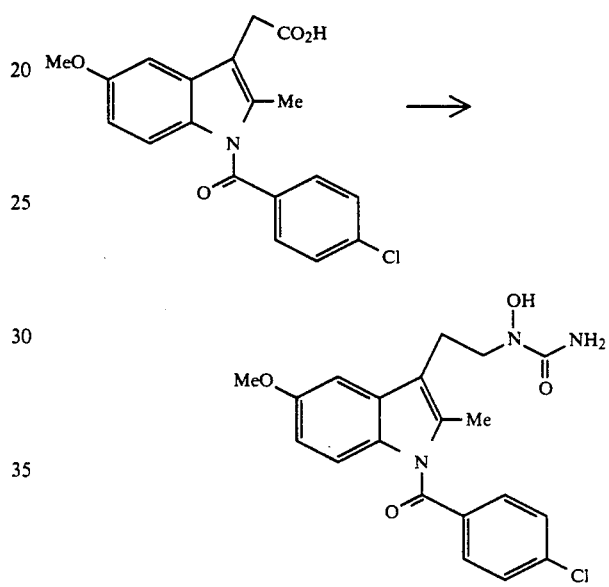

The above-named compound was prepared in the following manner as an example of the compounds of the present invention according to Scheme 2. Indomethacin (10 g, 28.0 mmole) was dissolved in dry THF (50 mL), cooled to 0° C. under a nitrogen atmosphere, and BH₃.THF (69 mL of a 1M solution in THF, 69 mmole) added slowly over 1 hour. After the addition was complete, the cooling bath was removed and the reaction stirred for 0.5 hour at room temperature. The reaction was quenched by cooling to 0° C. and slowly adding H₂O (80 mL). The volatiles were removed in vacuo from the quenched reaction solution and the resulting golden liquid purified by chromatography (silica gel, 75% ethyl acetate/hexanes) to give 7.2 g (74%) of the alcohol 16.1 as a yellow oil.

A solution of the alcohol 16.1 (7.12 g, 20.7 mmole), N,O-di-(t-butyloxycarbonyl)hydroxylamine (5.80 g, 24.9 mmole), and triphenylphosphine (7.06 g, 26.92 mmole) in dry THF (60 mL) was cooled to −10° C. under a nitrogen atmosphere. To the reaction solution was added diethyl azodicarboxylate (DEAD) (4.2 mL, 26.9 mmole) in THF (20 mL) over 20 minutes. The reaction was stirred 0.5 hour at −10° C. and the volatiles removed in vacuo. Chromatography (silica gel, 50% ethyl acetate/hexanes) provided 16.2 (12.6 g) as a yellow foam.

Deprotection was carried out by treating 16.2 (12.6 g, 91% pure, 20.71 mmole) in dichloromethane (50 mL)

with trifluoracetic acid (50 mL) at room temperature for 0.5 hour. The reaction was quenched by pouring the reaction solution into excess saturated aqueous Na$_2$CO$_3$. The resulting two-phased solution was extracted twice (ethyl acetate). The combined organic layers were washed twice (brine), dried (anhydrous Na$_2$SO$_4$), filtered and concentrated in vacuo. Chromatography (silica gel, 70% ethyl acetate/hexanes) gave 3.16 g (8.81 mmole, 43%) of the free hydroxylamine 16.3.

Compound 16.3 (0.60 g, 1.67 mmole) was converted to the title compound by treatment with trimethylsilylisocyanate (0.15 mL, 2.51 mmole) following the procedure described in Example 1. Recrystallization from THF/hexanes provided the desired compound (0.30 g, 43%). m.p.=172°–173.5° C.; $^1$H NMR (300 MHz, DMSO-d$_6$) 9.39 (s, 1H), 7.68 (AB, J=9 Hz, 2 H), 7.63 (AB, J=9 Hz, 2 H), 7.09 (d, J=2.5 Hz, 1 H), 6.98 (d, J=9 Hz, 1 H), 6.72 (dd, J=9, 2.5 Hz, 1 H), 6.33 (s, 2 H), 3.78 (s, 3 H), 3.52 (br t, J=7.5 Hz, 2 H), 2.86 (br t, J=7.5 Hz, 1 H), 2.18 (s, 3 H); MS (DCI) (M+H)$^+$=402, (M+NH$_4$)$^+$=419. [Analysis calc'd for C$_{20}$H$_{20}$N$_3$O$_4$Cl: C, 59.78; H, 5.02; N, 10.46. Found: C, 59.88; H, 5.13; N, 10.21.]

EXAMPLE 17

N-hydroxy-N-[2-(4-(2-methylpropyl)phenyl)propyl] urea (Formula 1,

Z=2-(4-(2-methylpropyl)phenyl)propyl, R$_1$=NH$_2$, M=H, Y=O)

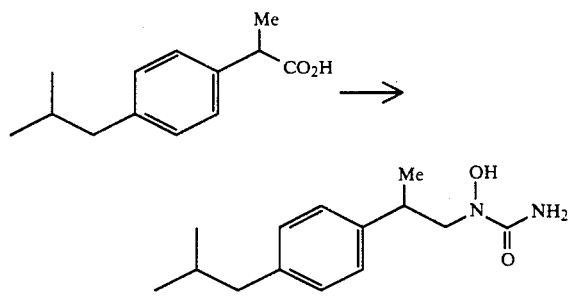

The above-named compound was prepared in the following manner as a further example of the compounds of the present invention according to Scheme 2. To a solution of ibuprofen (5 g, 24.2 mmole) in THF (97 mL) at 0° C. under nitrogen was added BH3.THF (60.6 mL of a 1 M solution in THF, 60.6 mmole) over 1 hour. After the addition was complete, the cooling bath was removed and the reaction stirred at room temperature for 0.5 hour. The reaction was quenched by cooling to 0° C. and slowly adding H$_2$O (100 mL). The volatiles were removed in vacuo from the quenched reaction solution to give the corresponding alcohol 17.1 (4.7 g, 101%) as a colorless solid which was utilized without further purification.

A solution of the alcohol 17.1 (4.7 g, 24.4 mmole), N,O-di-(t-butyloxycarbonyl)hydroxylamine (6.78 g, 29.1 mmole), and triphenylphosphine (8.26 g, 31.5 mmole) in dry THF (100 mL) was cooled to −10° C. under a nitrogen atmosphere. To the reaction solution was added diethyl azodicarboxylate (DEAD) (4.96 mL, 31.5 mmole) in THF (20 mL) over 20 minutes. The reaction was stirred for 1 hour at −10° C. and the volatiles removed in vacuo. Chromatography (silica gel, 8% ethyl acetate/hexanes) provided intermediate 17.2 (8.87 g, 90%) as a clear oil.

Deprotection was carried out by treating 17.2 (8.87 g, 21.8 mmole) in dichloromethane (50 mL) at room temperature with trifluoroacetic acid (50 mL) for 10 minutes. The reaction was quenched by pouring the reaction solution into excess saturated aqueous Na$_2$CO$_3$. The resulting two-phased solution was extracted twice (ethyl acetate). The combined organic layers were washed twice (brine), dried (anhydrous Na$_2$SO$_4$), filtered and concentrated in vacuo to provide the free hydroxylamine 17.3 as a light tan oil (4.50 g, 100%) which was utilized without further purification.

The hydroxylamine 17.3 (0.50 g, 2.4 mmole) was converted to the title compound by treatment with trimethylsilylisocyanate (0.63 mL) following the procedure described in Example 1. Recrystallization from THF/hexanes provided the desired compound (0.38 g, 67%) as a colorless solid. m.p.=140°–141° C.; $^1$H NMR (300 MHz, DMSO-d$_6$) 9.28 (s, 1 H), 7.14 (AB, J=8.5 Hz, 2 H), 7.06 (AB, J=8.5 Hz, 2 H), 6.23 (br s, 2 H), 3.53 (dd, J=14, 9 Hz, 1 H), 3.47 (dd, J=14, 6 Hz, 1 H), 3.05 (hextet, J=7 Hz, 1 H), 2.39 (d, J=7 Hz, 3 H), 1.79 (septet, J=7 Hz, 1 H), 1.17 (d, J=7 Hz, 3 H), 0.86 (d, J=7 Hz, 6 H); MS (DCI) (M+NH$_4$)$^+$=268, (2 M+H)$^+$=501. [Analysis calc'd for C$_{14}$H$_{22}$N$_2$O$_2$: C, 67.17; H, 8.86; N, 11.19. Found: C, 67.08; H, 9.16; N, 11.11.]

EXAMPLE 18

N-hydroxy-N-[2-(4-benzyloxy-3-chlorophenyl)ethyl] urea (Formula 1,

Z=2-(4-benzyloxy-3-chlorophenyl)ethyl, R$_1$=NH$_2$, M=H, Y=O)

The above-compound is prepared by the method of Example 16 except that benzofenac is used instead of indomethacin.

EXAMPLE 19

N-hydroxy-N-[1-(4-(2'-methylpropyl)phenyl)propyl] urea (Formula 1,

Z=1-(4-(2'-methylpropyl)phenyl)propyl, R$_1$=NH$_2$, M=H, Y=O)

The above-named compound is prepared by the method of Example 1 except that butibufen is used instead of ibuprofen.

EXAMPLE 20

N-hydroxy-N-[2-(4-(2-methylpropyl)phenyl)butyl] urea (Formula 1, Z=2-(4-(2-methylpropyl)phenyl)butyl, R$_1$=NH$_2$, M=H, Y=O)

The above-named compound is prepared by the method of Example 17 except that butibufen is used instead of ibuprofen.

EXAMPLE 21

N-hydroxy-N-(fluoren-2-yl)ethyl urea (Formula 1, Z=fluoren-2-ylethyl, R$_1$=NH$_2$, M=H, Y=O)

The above-named compound is prepared by the method of Example 1 except that cycloprofen is used instead of ibuprofen.

EXAMPLE 22

N-hydroxy-N-[2-(N-cinnamoyl-5-methoxy-2-methyl-[1H]-indol-3-yl)ethyl] urea (Formula 1, Z=2-(N-cinnamoyl)-5-methoxy-2-methyl-[1H]-indol-3-yl)ethyl, $R_1=NH_2$, M=H, Y=O)

The above-named compound is prepared by the method of Example 16 except that cinmetacin is used instead of indomethacin.

EXAMPLE 23

N-hydroxy-N-(6-chloro-5-phenylindanyl) urea (Formula 1, Z=6-chloro-5-phenylindan-1-yl, $R_1=NH_2$, M=H, Y=O)

The above-named compound is prepared by the method of Example 1 except that clidanac is used instead of ibuprofen.

EXAMPLE 24

N-hydroxy-N-[2-(2-(2,4-dichlorophenoxyphenyl))ethyl] urea (Formula 1, Z=2-(2-(2,4-dichlorophenoxyphenyl))ethyl, $R_1=NH_2$, M=H, Y=O)

The above-named compound is prepared by the method of Example 16 except that fenclofenac is used instead of indomethacin.

EXAMPLE 25

N-hydroxy-N-(4-phenoxyphenyl)ethyl urea (Formula 1, Z=4-phenoxyphenyl)ethyl, $R_1=NH_2$, M=H, Y=O)

The above-named compound is prepared by the method of Example 1 except that fenoprofen is used instead of ibuprofen.

EXAMPLE 26

N-hydroxy-N-(3-phenylbenzo[b]furan-7-yl)ethyl urea (Formula 1, Z=3-phenylbenzo[b]furan-7-yl)ethyl, $R_1=NH_2$, M=H, Y=O)

The above-named compound is prepared by the method of Example 1 except that furaprofen is used instead of ibuprofen.

EXAMPLE 27

N-hydroxy-N-[2-(2,3-dihydro-2-ethylbenzo[b]furan-5-yl)ethyl] urea (Formula 1, Z=2-(2,3-dihydro-2-ethylbenzo[b]furan-5-yl)ethyl, $R_1=NH_2$, M=H, Y=O)

The above-named compound is prepared by the method of Example 16 except that furofenac is used instead of indomethacin.

EXAMPLE 28

N-hydroxy-N-(4-(N-1,3-dihydro-1-oxoisoindolyl)-phenyl)ethyl urea (Formula 1, Z=4-(N-1,3-dihydro-1-oxoisoindolyl)phenyl)ethyl, $R_1=NH_2$, M=H, Y=O)

The above-named compound is prepared by the method of Example 1 except that indoprofen is used instead of ibuprofen.

EXAMPLE 29

N-hydroxy-N-[1-(4-(2'-methylpropyl)phenyl)ethyl] thiourea (Formula 1, Z=1-(4-(2-methylpropyl)phenyl)ethyl, $R_1=NH_2$, M=H, Y=S)

The title compound was prepared by the method of Example 1. Thus hydroxylamine 1.4 (0.25 gm, 1.3 mmol) was treated with trimethylsilylisothiocyanate (0.34 gm, 2.56 mmol) in THF (10 mL) at 23° C. Processing the reaction as described in Example 1, chromatographic purification (30 gm silica gel, 35% ethyl acetate/hexanes) and recrystallization from ether/hexanes provided the title compound (70 mg, 22%) as a colorless solid. m.p.=153.5°–154.5° C.; $^1$H NMR (300 MHz, DMSO-d$_6$) δ9.59(br s, 1H), 7.7 (br s, 1H), 7.37 (br s, 1H), 7.27 (d, J=9.0 Hz, 2H), 7.08 (d, J=9.0 Hz, 2H), 6.53 (q, J=7.0 Hz, 1H), 2.41 (d, J=8.0 Hz, 2H), 1.81 (br nonet, J=7.0 Hz, 1H), 1.43 (d, J=7.0 Hz, 3H), 0.86 (d, J=7.0 Hz, 6H); MS (M+H)$^+$=253.

Analysis calc'd for $C_{13}H_{20}N_2OS$: C, 61.87; H, 7.99; N, 11.10; Found: C, 62.05; H, 8.02; N, 11.12.

EXAMPLE 30

N-hydroxy-N-[1-(4-(2'-methylpropyl)phenyl)ethyl] ethoxycarbamate. (Formula 1, Z=1-(4-(2-methylpropyl)phenyl)ethyl, $R_1=OEt$, M=H, Y=O)

The title compound was prepared by the method of Example 1. Thus hydroxylamine 1.4 (0.25 gm, 1.3 mmol) and triethylamine (0.23 mL, 1.7 mmol) in ether (10 mL) were treated with ethyl chloroformate (0.0.14 mL, 1.42 mmol) at 0° C. Processing the reaction as described in Example 1 and chromatographic purification (30 gm silica gel, 10% ethyl acetate/hexanes), provided the title compound (181 mg, 53%). $^1$H NMR (300 MHz, DMSO-d$_6$) δ9.19 (s, 1H), 7.23 (d, J=8.0 Hz, 2H), 7.07 (d, J=8.0 Hz, 2H), 5.18 (q, J=7.0 Hz, 1H), 4.06 (dq, J=2.0, 7.0, 7.0, 7.0 Hz, 2H), 2.41 (d, J=7.0 Hz, 2H), 1.81 (nonet, J=7.0 Hz, 1H), 1.43 (d, J=7.0 Hz, 3H), 1.28 (t, J=7.0 Hz. 3H), 0.87 (d, J=7.0 Hz, 6H); MS (M+H)$^+$=266. HRMS calc'd for $C_{15}H_{23}NO_3$: MW=265.1677; Found: MW=265.1669.

EXAMPLE 31

N-hydroxy-N-[1-(4-(2'-methylpropyl)phenyl)ethyl] thioethylcarbamate. (Formula 1, Z=1-(4-(2-methylpropyl)phenyl)ethyl, $R_1=SEt$, M=H, Y=O)

The title compound was prepared by the method of Example 1. Thus hydroxylamine 1.4 (0.25 gm, 1.3 mmol) and triethylamine (0.23 mL, 1.7 mmol) in ether (10 mL) were treated with chlorothioethylformate (0.18 gm, 1.42 mmol) at 0° C. Processing the reaction as described in Example 1 and recrystallization from hexanes provided the title compound (165 mg, 45%) as a colorless solid. m.p.=82.5°–84.5° C.; $^1$H NMR (300 MHz, DMSO-d$_6$) δ9.93(br s, 1H), 7.21 (d, J=9.0 Hz, 2H), 7.08 (d, J=9.0 Hz, 2H), 5.42 (q, J=7.0 Hz, 1H), 2.70 (dq, J=2.0, 7.0, 7.0, 7.0 Hz, 2H), 2.41 (d, J=8.0 Hz, 2H), 1.81 (br nonet, J=7.0 Hz, 1H), 1.44 (d, J=7.0 Hz, 3H), 1.1.27 (t, J=7.0 Hz, 3H) 0.86 (d, J=7.0 Hz, 6H); MS (M+H)$^+$=282, (M+NH$_4$)$^+$=299. Analysis calc'd for $C_{15}H_{23}NO_2S$: C, 64.02; H, 8.24; N, 4.98; Found: C, 63.96; H, 8.16; N, 4.94.

EXAMPLE 32

N-hydroxy-N-[2-(N-(4-chlorobenzoyl)-5-methoxy-2-methyl-[1H]-indol-3-yl)ethyl]-N'-methyl urea (Formula 1, Z=2-(N-(4-chlorobenzoyl)-5-methoxy-2-methyl-[1H]-indol-3-yl)ethyl, $R_1$=NHMe, M=H, Y=O)

The title compound was prepared by the method of Example 1. Thus hydroxylamine 16.3 (0.60 gm, 1.67 mmol) was treated with N-methylisocyanate (0.15 mL, 2.51 mmol) in dry THF (7 mL). Processing the reaction as described in Example 1 and recrystallization from THF/hexanes provided the title compound (300 mg, 43%) as a faintly yellow solid. m.p.=172°-173.5° C.; $^1$H NMR (300 MHz, DMSO-$d_6$) δ9.32 (s, 1 H), 7.68 (AB, J=9 Hz, 2 H), 7.63 (AB, J=9 Hz, 2 H), 7.09 (d, J=2.5 Hz, 1 H), 6.94 (d, J=9 Hz, 1 H),6.89 (q, J=5.0 Hz, 1H), 6.72 (dd, J=9, 2.5 Hz, 1 H), 6.33 (s, 2 H), 3.78 (s, 3 H), 3.52 (br t, J=7.5 Hz, 2 H), 2.86 (br t, J=7.5 Hz, 1 H), 2.58 (d, J=5.0 Hz, 3H), 2.18 (s, 3 H); MS (DCI) $(M+H)^+$=416, $(M+NH_4)^+$=433; Analysis calc'd for $C_{21}H_{22}N_3O_4Cl$: C, 60.65; H, 5.33; N, 10.10. Found: C, 60.93; H, 5.39; N, 9.95.

EXAMPLE 33

In vitro inhibition of 5-lipoxygenase

The In vitro effect of the compounds of the present invention on 5-lipoxygenase activity was evaluated using the 20,000xg supernatant from homogenized RBL-1 cells in a manner similar to that described by Dyer and coworkers in *Fed. Proc., Fed. Am. Soc. Exp. Biol.* 43:1462A (1984). IC$_{50}$ values (i.e., concentrations of the compounds producing 50% enzyme inhibition) were calculated by linear regression analysis of percentage inhibition versus log inhibitor concentration plots. The values so computed are shown in Table 1, below, and demonstrate the unexpectedly high level of lipoxygenase inhibition produced by the compounds of the invention.

TABLE 1

| Example | IC$_{50}$ (10$^{-6}$ M) |
|---|---|
| 1 | 0.64 |
| 2 | 0.43 |
| 3 | 0.70 |
| 4 | 0.60 |
| 5 | 0.70 |
| 16 | 0.40 |
| 17 | 0.20 |
| 29 | <0.40 |
| 30 | <0.40 |
| 31 | 0.20 |
| 32 | 0.20 |

EXAMPLE 34

In vivo Inhibition of Leukotriene Biosynthesis

The in vivo inhibition of leukotriene biosynthesis by the compounds of the present invention was evaluated in the following manner. The effect of the compounds after oral administration was determined using a rat peritoneal anaphylaxis model in a manner similar to that described by Young and coworkers in *Fed. Proc., Fed. Am. Soc. Exp. Biol.* 44:1185 (1985). According to this model rats were injected intraperitoneally (IP) with rabbit antibody to bovine serum albumin (BSA) and three hours later injected IP with BSA to induce an antigen-antibody response. Rats were sacrificed 15 minutes after this challenge and the peritoneal fluids were collected and analyzed for leukotriene levels. Test compounds were administered by gavage (PO) one hour prior to the antigen challenge. Percent inhibition values were determined by comparing the treatment group to the mean of the control group. The results of this assay, shown below in Table 2, demonstrate that the compounds of this invention are orally effective in preventing the in vivo biosynthesis of leukotrienes.

TABLE 2

| Example | In vivo Inhibition of Leukotriene Biosynthesis |
|---|---|
| 2 | 66% at 200 μmol/kg PO |
| 3 | 39% at 200 μmol/kg PO |
| 5 | 62% at 200 μmol/kg PO |
| 32 | 42% at 200 μmol/kg PO |

What is claimed is:

1. A compound of the formula

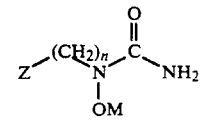

wherein
$R_1$ is selected from
(1) hydrogen;
(2) —NR$_2$R$_3$, —OR$_2$ or —SR$_2$ where R$_2$ and R$_3$ are independently selected from
  hydrogen,
  alkyl of from one to twelve carbon atoms,
  aryl, selected from phenyl and 1- or 2-naphthyl,
  alkylaryl wherein the alkyl portion is as defined above;
(3) C$_1$–C$_8$ alkyl;
(4) C$_2$–C$_8$ alkenyl;
(5) aralkyl wherein the aryl and alkyl portions are as defined above;
(6) cycloalkyl of from three to eight carbon atoms; and
(7) a group selected from (3)–(6) above substituted with one group selected from
  C$_1$–C$_6$ alkoxy,
  halo,
  cyano,
  amino,
  carboxy,
  —COX,
  —OCOX, and
  —NHCOX
  where X is selected from
  alkoxy of from one to four carbon atoms,
  amino,
  alkylamino, dialkylamino, alkyl and aryl wherein alkyl at each occurence is of from one to twelve carbon atoms, and aryl is selected from phenyl and 1- or 2 naphthyl;
Y is selected from sulfur and oxygen;
n is an integer selected from 0 and 1;
M is hydrogen or a phramaceutically acceptable cation;
Z is a residue of a non-steroidal antiinflammatory drug of the general formula Z—COOH selected from the group consisting of
benzofenac,
bucloxic acid,
butibufen,
cicloprofen, cinmetacin,
clinidacac,
diclofenac,
fenbufen,
fenclofenac,
fenoprofen,
ibufenac,
ibuprofen,
keotprofen,
naproxen, and
sulindac, or a pharmaceutically acceptable salt thereof 2. The compound of claim 1 wherein R1 is selected from amino, methylamino, phenylamino, methyl, ethoxy and tert-butylthiol.

3. The compound of claim 1 wherein Y is oxygen.

4. A compound selected from the group consisting of:
N-hydroxy-N-(1-(4-(2'-methylpropyl)phenyl)ethyl)urea,
N-hydroxy-N-1-(6-methoxynaphthalen-2-yl)ethyl urea,
N'-methyl-N-hydroxy-N-1-(4-(2'-methylpropyl)phenyl)ethyl urea,
N'-methyl-N-hydroxy-N-1-(6-methoxynaphthalen-2-yl)ethyl urea,
N-hydroxy-N-1-(6-methoxynaphthalen-2-yl)ethyl urea potassium salt,
N-hydroxy-N-1-(6-methoxynaphthalen-2-yl)ethyl thiourea,
N-hydroxy-N-1-(6-methoxynaphthalen-2-yl)ethyl-N'-phenyl urea,
N-hydroxy-N-1-(6-methoxynaphthalen-2-yl)ethyl-N'-benzyl urea,
N-hydroxy-N-(2-(4-(2-methylpropyl)phenyl)propyl)urea,
N-hydroxy-N-(2-(4-benzyloxy-3-chlorophenyl)ethyl)urea,
N-hydroxy-N-(1-(4-(2'-methylpropyl)phenyl)propyl)urea,
N-hydroxy-N-(2-(4-(2-methylpropyl)phenyl)butyl)urea,
N-hydroxy-N-fluoren-2-ylethyl urea,
N-hydroxy-N-(2-(2-(2,4-dichlorophenoxyphenyl))ethyl)urea,
N-hydroxy-N-(4-phenoxyphenyl)ethyl urea,
N-hydroxy-N-(1-(4-(2'-methylpropyl)phenyl)ethyl)thiourea, or a pharmaceutically acceptable salt thereof.

5. A pharmaceutical composition comprising a therapeutically effective amount of a compound of claim 1 in combination with a pharmaceutically acceptable carrier.

6. A method of inhibiting lipoxygenase enzymes in a mammal in need of such treatment comprising administering to the mammal a therapeutically efective amount of a compound of claim 1.

* * * * *